United States Patent [19]
Wu

[11] Patent Number: 5,120,301
[45] Date of Patent: Jun. 9, 1992

[54] SELF-CONTAINED SWAB

[76] Inventor: Shuenn R. Wu, No. 18, Alley 1, Lane 380, Sec. 4, Hsi Men Rd., Tainan, Taiwan

[21] Appl. No.: 539,012

[22] Filed: Jun. 15, 1990

[51] Int. Cl.$^5$ .......................................... A61M 35/00
[52] U.S. Cl. .......................................... 604/3; 604/1
[58] Field of Search .......................................... 604/1-3; 401/132-134

[56] References Cited

U.S. PATENT DOCUMENTS

| | | | |
|---|---|---|---|
| 3,774,609 | 11/1973 | Schwartzman | 604/3 |
| 4,415,288 | 11/1983 | Gordon et al. | |
| 4,608,968 | 9/1986 | Rosofsky | 604/1 X |
| 4,747,719 | 5/1988 | Parkin | 604/1 X |
| 4,854,760 | 8/1989 | Pike et al. | 604/3 X |
| 4,957,385 | 9/1990 | Weinstein | 604/3 X |

Primary Examiner—David Isabella
Assistant Examiner—Elizabeth M. Burke

[57] ABSTRACT

A self-contained swab includes a hollow stick, one or both ends of which is formed with a fluid storing chamber separated from the stick by a transverse wall and the fluids stored within sealed by a thin membrane. The stick is further formed with two annular rings in the vicinity of the fluid storing chamber. A socket means includes a clamping end by means of which the socket means is couplable with the stick and slidable between the two annular rings. The other end of the socket means, on which a nonwoven cottom mass is carried, is formed with an inwardly projecting prong. The prong impales the thin membrane releasing the fluid when the socket means is slid back along the stick from the second to the first annular ring. The fluid absorbed by the cotton mass can then be appropriately applied.

1 Claim, 4 Drawing Sheets

SELF-CONTAINED SWAB

BACKGROUND OF THE INVENTION

The present invention relates generally to small swabs. More particularly, the present invention relates to self-contained swabs which are capable of storing fluids to be applied by the swab.

Small swabs employed in wiping and applying fluids are widely known. For example, such swabs are employed in surgery, in the wiping of tissue and the application of medication thereto in the cleaning and lubricating of delicate equipment and machinery as well as in many other applications. A common form of swab which is generally used comprises a stick around one or both ends is of which wound and to which is adhered a teardrop-shaped nonwoven cotton mass that projects beyond the end of the stick.

In practical use of the above-mentioned swabs, fluids before application must first be allowed to be absorbed by the swab by immersion of the stick supported nonwoven cotton mass in a fluid container. The fluid container storing the fluids or drugs, then, must not only be kept handy, which can be cumbersome due to the frequently required opening and closing of the fluid container. However, the frequent opening and closing of the fluid container exacerbates problems such as contamination of the fluid or drug and to the user's hands more likely to occur.

To mitigate and/or obviate the above-mentioned drawback as well as to provide an improved swab, the present invention has introduced a socket means disposed between the stick and the cotton mass. The stick comprises a body portion and a fluid storing chamber that is sealed by a thin membrane. The socket means comprises a clamping end for coupling with the stick and a prong end for impaling the thin membrane when the socket means is slid relative to the stick.

SUMMARY OF THE INVENTION

A primary objective of the present invention is to provide a self-contained swab which comprises a stick having a fluid storing chamber and a socket means, on which the cotton mass is carried, for releasing the fluid when a relative sliding movement between the socket means and the stick is effected.

Another objective of the present invention is to provide a self-contained swab which, in use, does not require cooperation with external fluid containers in which fluids and drugs are stored.

A further objective of the present invention is to provide a self-contained swab in which various fluids or drugs can be mixed and stored in a desired proportion.

A still further objective of the present invention is to provide a self-contained swab comprising a fluid storing chamber which is disposable, i.e. used only one time so that contamination of the fluid or drug and exposure to the user's skin is reduced.

Another objective of the present invention is to provide a self-contained swab which is easy in application.

Further objectives and advantages of the present invention will become apparent as the following description proceeds, and the features of novelty which characterize the invention will be pointed out with particularity in the claims annexed to and forming a part of this invention.

DETAILED DESCRIPTION OF THE PREFERRED EMBODIMENT

Figure 1:
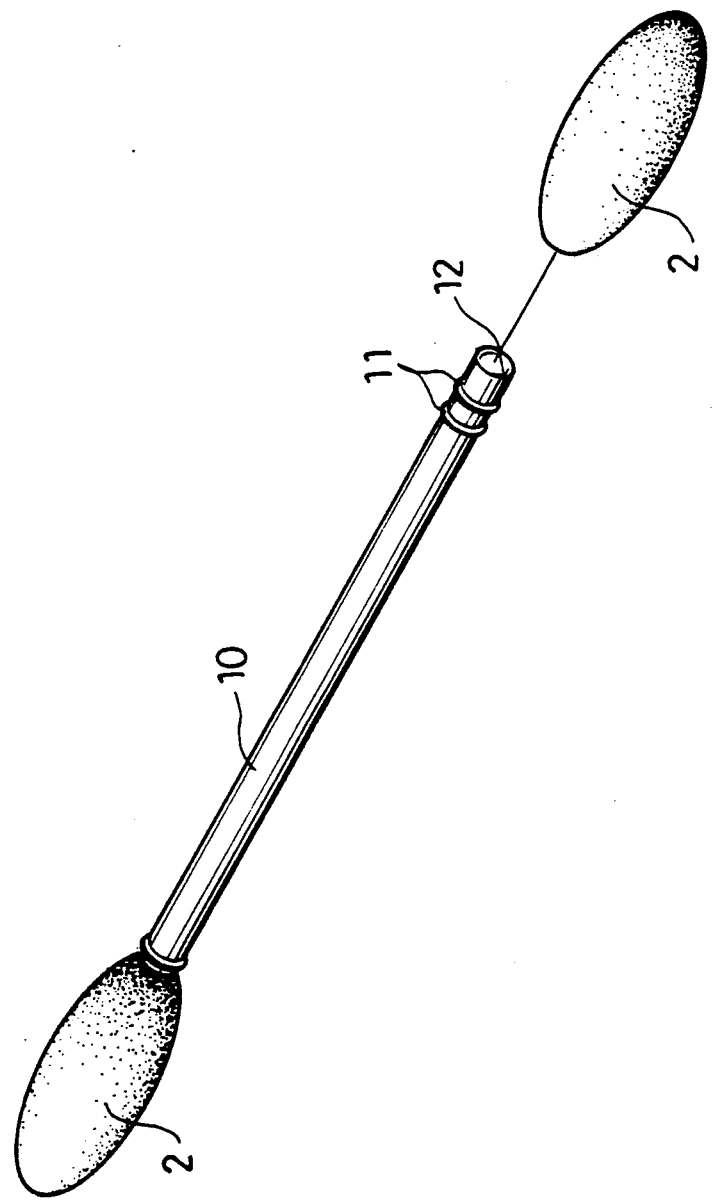
FIG. 1 is an exploded view of a self-contained swab in accordance with the present invention.

FIG. 1 shows the hollow stick 10 formed at an end thereof with two annular rings 11 and sealed by a thin membrane 12. A cotton mass 2 is carried on the end of the hollow stick 10 such that only one of the two annular rings 11 is left exposed.

Figure 2:
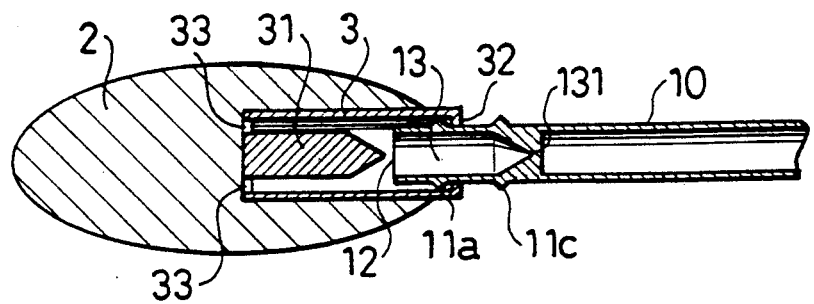
FIG. 2 is a partial sectional side view of FIG. 1.

As shown in FIG. 2, the hollow stick 10 is furthermore formed at an end thereof with a fluid chamber 13 which is separated from the stick portion by an annular wall 131. The hollow stick is easily manufactured and the fluid storing chamber 13 filled with drugs, antiseptic, or the like, and then antisceptically sealed with the thin membrane 12. The cotton mass 2 is then carried on the end of the hollow stick 10 such that pressure applied to the cotton mass 2 punctures the thin membrane 12 allowing fluid stored in the fluid storing chamber 13 to be absorbed by the cotton mass 2. The fluid can then be antisceptically applied to the patient's injuries.

The cotton mass 2 is carried on a socket means 3 which couples with the stick 10. The socket means 3 is essentially a hollow cylinder formed at an end thereof with a clamping end 32 which slidably grips the stick 10 such that the socket means 3 is slidable along the stick 10 between a first annular ring 11a and a second annular ring 11b formed thereon.

The other end of the socket means is formed with an inwardly projecting prong 31 for impaling the thin membrane 12 when the socket means 3 is slid back along the stick 10 from the second annular ring 11b to the first annular ring 11a.

Figure 3:
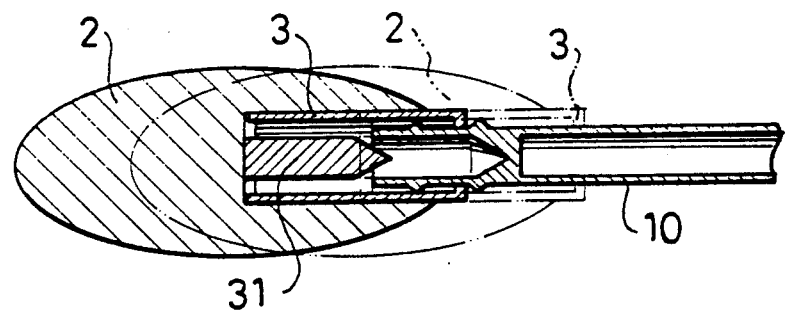
FIG. 3 is a view similar to FIG. 2 showing the sliding action of the socket means during use.

FIG. 2 shows that, before use of the swab, the thin membrane 12 serves to both contain and preserve the fluid within the storing chamber 13. The prong 31 therefore, either lightly rests on the thin membrane 12 or does not make contact with the membrane 12 at all. FIG. 3 shows that during use of the swab, the socket means 3 is slid back along the stick 10 causing the prong 31 to impale the thin membrane 12 thus releasing the fluid contained within the storing chamber 13. Perforations 33 in the prong end of the socket means 3 allow the fluid to burst therefrom and be absorbed by the cotton mass 2. The drug then can be properly applied.

FIG. 3 also shows that the cotton mass 2 can be forced or moved to slide over the second annular ring 11b till such a position schematically indicated by phantom lines that the prong 31 makes contact with the storing chamber 13 and stopped there. This facilitates the outflowing of the fluid contained within the storing chamber 13.

Figure 4:
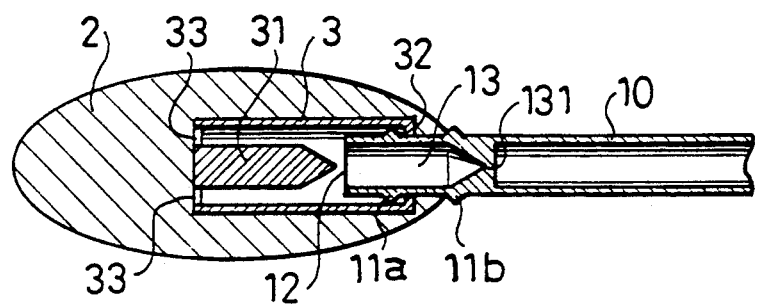
FIG. 4 shows an alternative arrangement of a cotton mass of another embodiment in accordance with the present invention.

It is noted that while the cotton mass 2 of the above embodiment encompasses only a portion of the socket means 3, the socket means 3 can be wholly enclosed by the cotton mass 2 in a manner as FIG. 4 shows. This arrangement will be effective and advantageous in absorption of fluid possibly leaking from the contact portion between the socket means 3 and the outer wall of the fluid storing chamber 13.

Figure 5:
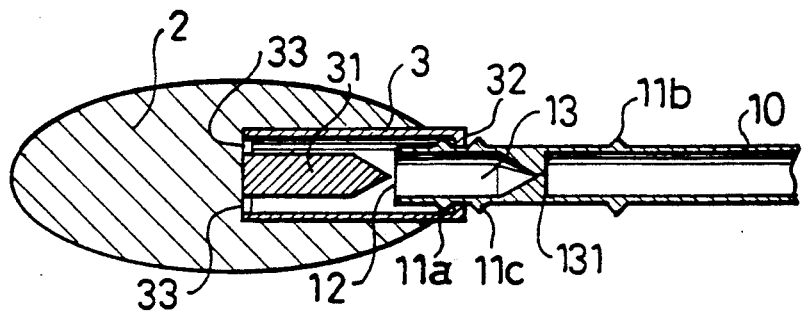
FIG. 5 is partial sectional side view of a self-contained swab showing another embodiment of the invention.
Figure 6:
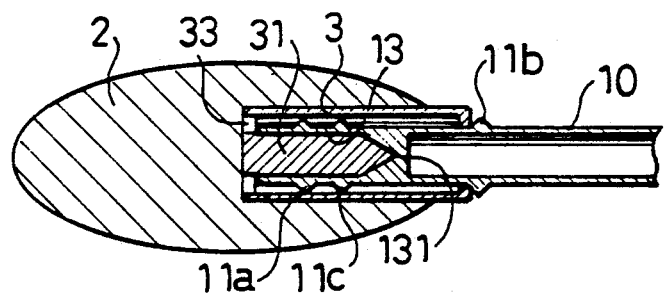
FIG. 6 is a view similar to FIG. 5 showing the sliding action of the socket means during use.

FIGS. 5 and 6 show another embodiment of the self-contained swab of the invention in which a third annular ring 11c is further disposed between the first and second annular rings 11a and 11b. The third annular ring 11c is arranged adjacent to the first annular ring 11a so that the two annular rings 11a and 11c cooperate each other to define a position for the socket means 3 before use. The positioning function the first and third annular rings 11a and 11c provide affords a secure mechanism which prevents the thin membrane 12 from being inadvertently break during transport. As can be understood, the socket means 3, the prong 31, the storing chamber 13, the first and second annular rings 11a and 11b are sized and shaped so that the fluid contained within the storing chamber 13 can be forced out to effect a better result.

While the present invention has been explained in relation to its preferred embodiment, it is to be understood that various modifications thereof will be apparent to those skilled in the art upon reading this specification. Therefore, it is to be understood that the invention disclosed herein is intended to cover all such modifications as shall fall within the scope of the appended claims.

I claim:

1. A self-contained swab comprising:
   a stick having a cylindrical wall having an inner and outer surfaces and comprising a body portion and end portions, at least one of said end portions providing a fluid storing chamber and having a sealing membrane over an outer end of said end portion, said chamber being separated from said body portion by a transverse wall, said fluid storing chamber being defined by said transverse wall, a portion of said inner surface of said cylindrical wall and said sealing membrane, the outer surface of said cylindrical wall having thereabout a first annular ring and a second annular ring adjacent said one end portion;
   a socket on said stick comprising a clamping end and a perforated end, said perforated end having an inwardly extending portion to form a prong, said clamping end being engaged with said cylindrical wall of said stick and movable thereon between said first and second annular rings so that said prong is able to slidably penetrate said sealing membrane of said fluid storing chamber, thereby releasing fluids contained in said fluid storing chamber;
   a cotton mass secured on said socket, said cotton mass enveloping said socket; and
   a third annular ring on the outer surface of said cylindrical wall of said stick between said first and second annular rings and adjacent to said first annular ring so that said socket is retained between said first and third annular rings before use.

* * * * *